US008859517B2

(12) United States Patent  
Priori et al.

(10) Patent No.: US 8,859,517 B2
(45) Date of Patent: Oct. 14, 2014

(54) METHOD OF GENE TRANSFER FOR THE TREATMENT OF RECESSIVE CATECHOLAMINERGIC POLYMORPHIC VENTRICULAR TACHYCARDIA (CPVT)

(75) Inventors: Silvia G. Priori, Milan (IT); Carlo Napolitano, Milan (IT); Marco Denegri, Stradella (IT)

(73) Assignee: Fondazione Salvatore Maugeri Clinica del Lavoro e Della Riabilitazione, Pavia (IT)

( * ) Notice: Subject to any disclaimer, the term of this patent is extended or adjusted under 35 U.S.C. 154(b) by 0 days.

(21) Appl. No.: 13/569,490

(22) Filed: Aug. 8, 2012

(65) Prior Publication Data

US 2013/0059905 A1    Mar. 7, 2013

Related U.S. Application Data

(60) Provisional application No. 61/521,076, filed on Aug. 8, 2011.

(51) Int. Cl.
*A61K 48/00* (2006.01)

(52) U.S. Cl.
CPC .................................. *A61K 48/005* (2013.01)
USPC ...... 514/44 R; 424/93.2; 536/23.1; 435/320.1

(58) Field of Classification Search
CPC .............................. A61K 48/00; A61K 48/005
See application file for complete search history.

(56) References Cited

U.S. PATENT DOCUMENTS

| 2012/0252882 A1* | 10/2012 | Chuah et al. ................. 514/44 R |
| 2013/0059905 A1 | 3/2013 | Priori et al. |
| 2013/0197061 A1 | 8/2013 | Hohjoh et al. |

FOREIGN PATENT DOCUMENTS

EP             2177615 A1       4/2010

OTHER PUBLICATIONS

Strausberg et al. "Generation and initial analysis of more than 15,000 full-length human and mouse cDNA sequences." Proc. Natl. Acad. Sci. U.S.A. 99 (26), 16899-16903 (2002); Accession No. BC092229.*
Knollman et al., "Casq2 Deletion Causes Sarcoplasmic Reticulum Volume Increase, The Premature Ca 2+ release, and Cathecholaminergic Polymorphic Ventricular Tachycarida." The Journal of Clinical Investigation vol. 116, No. 9: 2510-2520, 2006.*
Rolf et al. Direct Submission. Cloning of human full-length CDS FLEXGene in Gateway(TM) recombinational vector system Aug. 2006 pp. 1-4.*
Lahat et al., "A Missense Mutation in a Highly Conserved Region of CASQ2 Is Associated with Autosomal Recessive Catecholamine-Induced Polymorphic Ventricular Tachycardia in Bedouin Families from Israel," Am. J. Hum. Genet. 69: 1378-1384, 2001.

Priori et al., "Mutations in the Cardiac Ryanodine Receptor Gene (hRyR2) Underlie Catecholaminergic Polymorphic Ventricular Tachycardia," American Heart Association Journals 103: 196-200, 2001.
Cerrone et al., "Bidirectional Ventricular Tachycardia and Fibrillation Elicited in a Knock-In Mouse Model Carrier of a Mutation in the Cardiac Ryanodine Receptor," American Heart Association Journals 96: e77-e82, 2005.
Knollmann et al., "Casq2 Deletion Causes Sarcoplasmic Reticulum Volume Increase, Premature $Ca^{2+}$ Release, and Catecholaminergic Polymorphic Ventricular Tachycardia," The Journal of Clinical Investigation vol. 116, No. 9: 2510-2520, 2006.
Liu et al., "Arrhythmogenesis in Catecholaminergic Polymorphic Ventricular Tachycardia: Insights From a RyR2 R4496C Knock-In Mouse Model," American Heart Association Journals 99: 292-298, 2006.
Bish et al., "Adeno-Associated Virus (AAV) Serotype 9 Provides Global Cardiac Gene Transfer Superior to AAV1, AAV6, AAV7, and AAV8 in the Mouse and Rat," Human Gene Therapy 19: 1359-1368, 2008.
Rizzi et al., "Unexpected Structural and Functional Consequences of the R33Q Homozygous Mutation in Cardiac Calsequestrin: A Complex Arrhythmogenic Cascade in a Knock in Mouse Model," American Heart Association Journals 103: 298-306, 2008.
Horowitz et al., "Clinical Trials Update AHA Congress 2010," Cardiovasc Drugs Ther 25: 69-76, 2011.
Denegri et al., "Adeno-associated viral gene delivery of calsequestrin 2 protects adult calsequestrin 2-R33Q knock-in mice from developing ventricular tachycardias," Core 4. Heart Rhythm Disorders and Resuscitation Science, Session Title: Calcium-Triggered Arrhythmia, Circulation. 2012; 126: A18712 (1 page).
Denegri et al., "Viral gene transfer is able to revert phenotypical manifestation of recessive catecholaminergic polymorphic ventricular tachycardia in highly symptomatic adult knock-in mice," Session: APS.502.03-Novel Cellular Therapies for Ischemic Heart Failure, Abstract No. 15777, Nov. 18, 2013 (1 page).
Denegri et al., "Viral gene transfer rescues arrhythmogenic phenotype and ultrastructural abnormalities in adult calsequestrin-null mice with inherited arrhythmias," Circ Res. 110(5):663-8 (2012). "In This Issue" Anthology (pp. e125-55) and online supplemental material (pp. 1-15) provided.
Faggioni et al., "Calsequestrin mutations and catecholaminergic polymorphic ventricular tachycardia," Author manuscript, available in PMC on Aug. 1, 2013, published in final edited form as: Pediatr Cardiol. 33(6):959-67 (2012).
Liu et al., "Abnormal propagation of calcium waves and ultrastructural remodeling in recessive catecholaminergic polymorphic ventricular tachycardia," Circ Res. 113(2):142-52 (2013). Supplemental material provided (pp. 1-11).
Liu et al., "Facilitated maturation of Ca2+ handling properties of human embryonic stem cell-derived cardiomyocytes by calsequestrin expression," Am J Physiol Cell Physiol. 297(1):C152-9 (2009).

(Continued)

*Primary Examiner* — Deborah Crouch
*Assistant Examiner* — Titilayo Moloye
(74) *Attorney, Agent, or Firm* — Clark & Elbing LLP

(57) ABSTRACT

The present invention concerns a method for the treatment of recessive Catecholaminergic Polymorphic Ventricular Tachycardia comprising delivering a gene into a cardiac cell.

10 Claims, 7 Drawing Sheets

(56) References Cited

OTHER PUBLICATIONS

Louch, "Mind the store: modulating Ca(2+) reuptake with a leaky sarcoplasmic reticulum," Cardiovasc Res. 98(2):165-8 (2013).

Miller et al., "Effects of calsequestrin over-expression on excitation-contraction coupling in isolated rabbit cardiomyocytes," Cardiovasc Res. 67(4):667-77 (2005).

Napolitano et al., "Catecholaminergic polymorphic ventricular tachycardia," Pagon RA, Adam MP, Ardinger HH, et al., editors. GeneReviews, Seattle (WA): University of Washington, Seattle, Oct. 14, 2004 (22 pages).

O'Brian et al., "Mass spectrometry of cardiac calsequestrin characterizes microheterogeneity unique to heart and indicative of complex intracellular transit," Author manuscript, available in PMC Jul. 29, 2002, published in final edited form as: J Biol Chem. 277(40):37154-60 (2002).

Praveen et al., "Gene therapy in cardiac arrhythmias," Indian Pacing Electrophysiol J. 6(2):111-8 (2006).

Terentyev et al., "Abnormal interactions of calsequestrin with the ryanodine receptor calcium release channel complex linked to exercise-induced sudden cardiac death," Circ Res. 98(9):1151-8 (2006). Online data supplement provided (pp. 1-21).

Viatchenko-Karpinski et al., "Abnormal calcium signaling and sudden cardiac death associated with mutation of calsequestrin," Circ Res. 94(4):471-7 (2004). Online supplement included.

* cited by examiner

METHOD OF GENE TRANSFER FOR THE TREATMENT OF RECESSIVE CATECHOLAMINERGIC POLYMORPHIC VENTRICULAR TACHYCARDIA (CPVT)

CROSS-REFERENCE TO RELATED APPLICATIONS

This application claims the benefit of U.S. Provisional Application No. 61/521,076, filed on Aug. 8, 2011, the contents of which are hereby incorporated by reference in their entirety.

FIELD OF THE INVENTION

The present invention concerns a method for the treatment of recessive catecholaminergic polymorphic ventricular tachycardia comprising delivering a gene into a cardiac cell.

STATE OF THE ART

Catecholaminergic Polymorphic Ventricular Tachycardia (CPVT) is an inherited ion channel disease characterized by high susceptibility to life threatening arrhythmias. Two forms of the disease have been described: the autosomal dominant variant and the autosomal recessive variant. The first is associated with mutations in the cardiac ryanodine receptor type 2 (RYR2) gene (1), while the autosomal recessive variant (2) is associated with mutations in the cardiac calsequestrin 2 (CASQ2) gene.

Clinical observations have shown that patients with the dominant form of CPVT develop bidirectional and polymorphic ventricular tachycardia in response to sympathetic activation, whereas their resting ECGs are unremarkable and heart structure is preserved. The RyR2 R4496C knock-in (KI) mutant mouse model was developed to closely mimic the human phenotype with atrial and ventricular arrhythmias during adrenergic stimulation (3). Using this model, it was demonstrated that arrhythmias are caused by delayed after depolarizations (DADs) and triggered activity (TA) (4). The recessive form of CPVT is associated with a more severe phenotype, but its pathophysiology is less well understood. Clinically, it was shown that patients with recessive CPVT have a high susceptibility to arrhythmias triggered by emotional stress or mild exercise. Furthermore, their arrhythmias are more often polymorphic rather than bidirectional and the response to therapy is often incomplete. Studies performed in homozygous $CASQ2^{R33Q/R33Q}$ mutant KI mice (5) and in CASQ2 knockout (KO) (8) mice support the view that recessive CPVT is also associated with a much more complex phenotype at the cellular level. $CASQ2^{R33Q/R33Q}$ mice develop ultrastructural rearrangements in the junctional sarcoplasmic reticulum (jSR) leading to a reduction in abundance and loss of spatial organization of crucial excitation-contraction (EC) proteins, including triadin (Tr) and junctin (JnC) (5). The need and importance is increasingly felt for an effective therapy in correcting all aspects of the functional derangements observed in the recessive form of CPVT.

SUMMARY OF THE INVENTION

The present invention concerns a method for the treatment of recessive Catecholaminergic Polymorphic Ventricular Tachycardia.

The invention will become fully clear from the following detailed description, given by way of a mere exemplifying and non limiting examples, to be read with reference to the attached drawing figures.

As will be further described in the detailed description of the invention, the method for the treatment of recessive Catecholaminergic Polymorphic Ventricular Tachycardia comprises the step of delivering a CASQ2 gene into a cardiac cell.

The authors have discovered that viral gene transfer to restore CASQ2 is highly effective in correcting all aspects of the functional derangements observed in the CASQ2 knockout (KO) mice. These results point at CASQ2 in the therapeutic approach based on viral gene transfer of wild-type (WT) CASQ2 into CPVT recessive hearts and the development of early phase human clinical trials.

BRIEF DESCRIPTION OF THE DRAWINGS

The characteristics and advantages of the present invention will be apparent from the detailed description reported below, from the Examples given for illustrative and non-limiting purposes, and from the annexed FIGS. 1-7.

Figure 1:
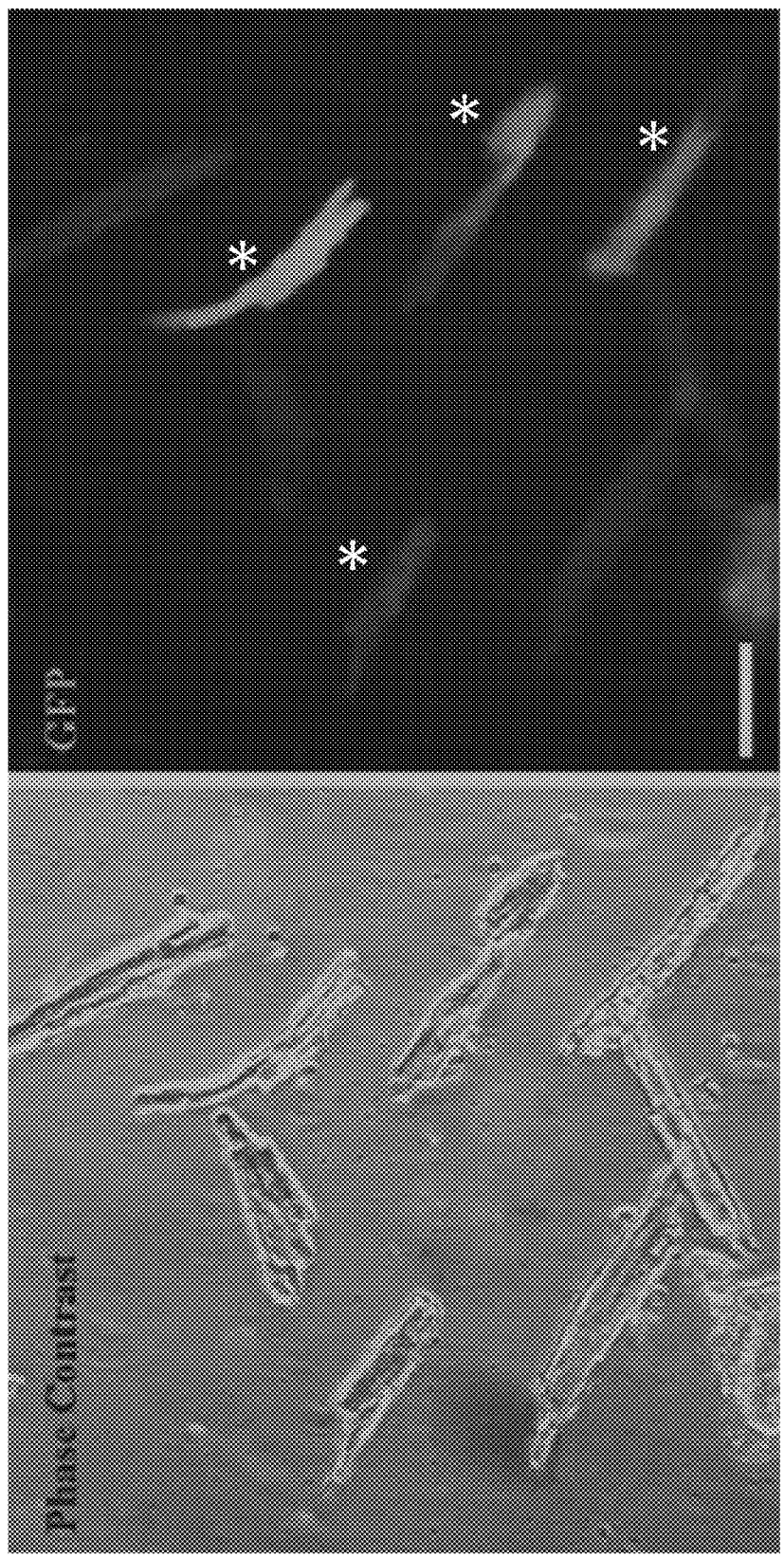
FIG. 1.

Infection efficiency of AAV2/9. Phase contrast (left panel) and GFP signal of the same adult myocytes isolated 20 weeks after infection with pAAV-2.1-WT-mCASQ2-IRES-GFP of a CASQ2-KO mouse. The stars are indicating the GFP positive cells corresponding to the Infected CASQ2-WT cardiomyocytes. Calibration bar=100 μm.

FIG. 2.

RealTime PCR performed on RNA extracted from adult myocytes isolated from Infected WT- and WT mice. The presented results indicates ~60% of RNA expression of the infected WT against the 100% of the WT mice.

FIG. 3.

Western blot in isolated cardiomyocytes extracted from adult WT (C57), CASQ2-KO and Infected WT mice. AAV2/9-WT-mCASQ2 infection restores level of expression not just of calsequestrin 2 but also of sister proteins, Tr and Jnc, other two components of the CRU. (Positive and negative signs indicate the presence or absence of the expressed proteins).

FIG. 4.

Localization analysis of protein distribution involved in Calcium Release Units (CRU) after infection of CASQ2-KO mice with WT-mCASQ2. The immunolabeling was performed with Ab anti RYR2, CASQ2, Tr and Jnc labeled in Red while in Green is possible to detect the expression of the reporter gene eGFP. Phase contrast in order to confirm the analysis on rod-shaped cells with clear cross striations. The "star" is indicating the GFP positive cells, while the head-arrows are indicating the classical staining of the proteins on the CRU. Calibration bar=20 μm.

FIG. 5.

Examples of triggered activity in isolated cardiomyocytes coming from negative GFP cells (C: not infected CASQ2-KO cells), positive GFP cells (B: infected with AAV2/9-WT-mCASQ2) and cells derived from WT mice (A).

FIG. 6.

Incidence of triggered activity in cardiomyocytes coming from negative GFP cells (GFP-NEG, not infected CASQ2-KO cells, no=12), positive GFP cells (INF-WT, infected with AAV2/9-WT-mCASQ2, no=16) and cells derived from WT mice (n°=16).

FIG. 7.

ECG recording in untreated CASQ2-KO mice showing the typical pattern of bidirectional VT upon epinephrine injection (lower panels to the left). Example of ECG recording from CASQ2-KO mice infected with AVV2/9-WT-mCASQ2 showing complete suppression of arrhythmias (Right panels).

DETAILED DESCRIPTION OF THE INVENTION

The present invention concerns a method for the treatment of recessive Catecholaminergic Polymorphic Ventricular Tachycardia.

In particular the method for the treatment of recessive CPVT according to the present invention comprises the step of delivering a CASQ2 gene into a cardiac cell.

The following abbreviations have been used in the present specification: CASQ2, calsequestrin 2; CPVT, Catecholaminergic Polymorphic Ventricular Tachycardia; CRU, calcium release unit; DAD, Delayed after depolarization; EC coupling, excitation-contraction coupling; ECG, electrocardiogram; EP, electrophysiology; I.P., intraperitoneal; ISO, isoproterenol; JnC, junctin; RYR2, ryanodine receptor type 2; KO, Knock Out; Tr, triadin; WT, Wild type; UTR, untranslated repeat region; IRES, internal ribosome entry site; INF WT mouse, homozygous CASQ2 KO mouse infected with pAAV 2/9-WT-mCASQ2-IRES-eGFP virus; VT, ventricular tachycardia.

In a preferred aspect the present invention relates to a method for efficient gene transfer for the treatment of recessive CPVT, wherein the CASQ2 gene is chosen from the group consisting of SEQ ID NO:1 and SEQ ID NO:2.

SEQ ID NO:1 corresponds to the coding sequence, without UTR sequences, of WT-murine CASQ2 (NM_009814.2; GI:157951699; GI:12373).

SEQ ID NO:2 corresponds to the human CASQ2 gene of NM_001232.3, GI:189011540; NM_001232.2, GI:119395726; GI: 845 and GI:209969794).

The method according to the present invention allows the correction of the bidirectional and polymorphic arrhythmias in patients with recessive CPVT by a viral gene transfer method by which a gene is delivered to the heart, preferably to the cardiac myocytes and expressed, whereby the normal and anti-arrhythmic contractile function of the heart is restored.

Such a method of CASQ2 gene transfer surprisingly restores the physiological levels of expression of the CASQ2 protein.

Furthermore the present inventors have found that the CASQ2 gene transfer restores the abundance and the spatial organization of crucial excitation-contraction (EC) proteins, such as for example triadin (Tr, NP_084002.2, GeneID: 76757) and junctin (JnC, NP_075553.2, GeneID: 65973). Abnormalities in morphology of calcium release units (CRUs), geometry of the EC coupling apparatus and imbalance of the CASQ2/Tr/JnC complex, results in abnormal propagation of $Ca^{2+}$ signaling.

The data already collected support the idea that viral gene transfer of WT CASQ2 ameliorates the ultrastructural abnormalities and the associated $Ca^{2+}$ wave fragmentation leading to an anti-arrhythmic effect. With the recent report of the CUPID clinical trial (6) establishing the safety of gene delivery using adeno-associated viruses in humans, the introduction of molecular therapy in the clinics is no longer a dream. The authors believe that this investigation may provide proof-of-principle for a molecular cure for recessive CPVT, which would be a highly impactful.

The CASQ2 gene of SEQ ID NO:1 and SEQ ID NO:2 is in the form of plasmid DNA, wherein said plasmid DNA comprises the CASQ2 gene inserted within the genome of a recombinant adenovirus.

In a preferred aspect the CASQ2 gene is inserted in a vector, preferably into a viral vector.

The CASQ2 gene may be advantageously inserted in the serotype 9 adeno-associated viral (AAV2/9) vector.

Viral gene transfer to restore CASQ2 is highly effective in correcting all aspects of the functional derangements observed in the CASQ2 KO mice.

Moreover, based on the fact that with correction of the CASQ2 defect there is a restoration of protein expression profiles at physiological levels, as well as a really strong reduction of DADs, triggered activity and a remarkable anti-arrhythmic effect in vivo, gene therapy with CASQ2 corrects all the abnormalities seen in recessive CPVT models.

This supports the potential therapeutic approach based on viral gene transfer of WT CASQ2 into CPVT recessive hearts and the development of early phase human clinical trials.

The method according to the present invention has advantageously allowed to restore the normal intracellular $Ca^{2+}$ storage and fluxes (between SR and cytosol) in cardiac cells, which are altered in patients with recessive CPVT. Interestingly, similar calcium handling abnormalities have been detected in heart failure thus creating the rational to test the same approach in this setting. Such a method comprising delivering a CASQ2 gene by viral gene transfer.

The observation that CASQ2 and the sister proteins Tr and JnC are involved in the scaffolding complex that ensures preservation of the ultrastructural architecture of the jSR, will impact our understanding of the functional role of the key proteins implicated in $Ca^{2+}$ homeostasis. This notion will advance not only understanding of CPVT but in fact will also be relevant to our understanding of acquired conditions characterized by deregulation of intracellular $Ca^{2+}$, such as heart failure. CASQ2 restores the intracellular $Ca^{2+}$ deregulation in CPVT patients.

EXAMPLES

Example 1

CASQ2 Gene was Cloning

The DNA of the murine WT CASQ2 gene was cloned into a bi-cistronic (pIRES) eukaryotic expression vector and subcloned into the multiple cloning site of pAAV2.1, serotype 9, -CMV-eGFP, containing the CMV promoter and green fluorescent protein as reporter gene (7)

Example 2

In Vivo Infection of Cardiac Murine Myocytes Using the AAV2/9 Vector for Efficient WT-mCASQ2 Gene Transfer We infected, by intraocular and intraperitoneal (I.P.) injection, neonatal (after birth, P2-P3) CASQ2 KO mice using 100 µl of serotype 9 adeno-associated viral (AAV2/9) vector containing WT-mCASQ2. The mice were monitored during their development and we did not observe any differences in comparison with the non infected littermates. To evaluate the infection efficiency in the mice, we performed a standard procedure of cardiac myocytes isolation by enzymatic digestion (4). The isolated cells were plated on coverslips and observed with epifluorescent microscope in order to assess the presence and the level of expression of the reporter gene, eGFP. The isolations were performed at 8, 10-12 and 20-30 weeks after infection. Best results were obtained after 20 weeks with a 50-60% of myocytes isolated from infected KO mice expressing the transgene as indicated by eGFP reporter expression (FIG. 1). Indeed, taking in considerations these results, the followed in vivo and in vitro experiments were achieved after 20 weeks after infection in CASQ2-KO and WT mice.

Example 3

Analysis of Expression of AAV2/9-WT-mCASQ2 in CASQ2-KO Infected Mice

Figure 2:
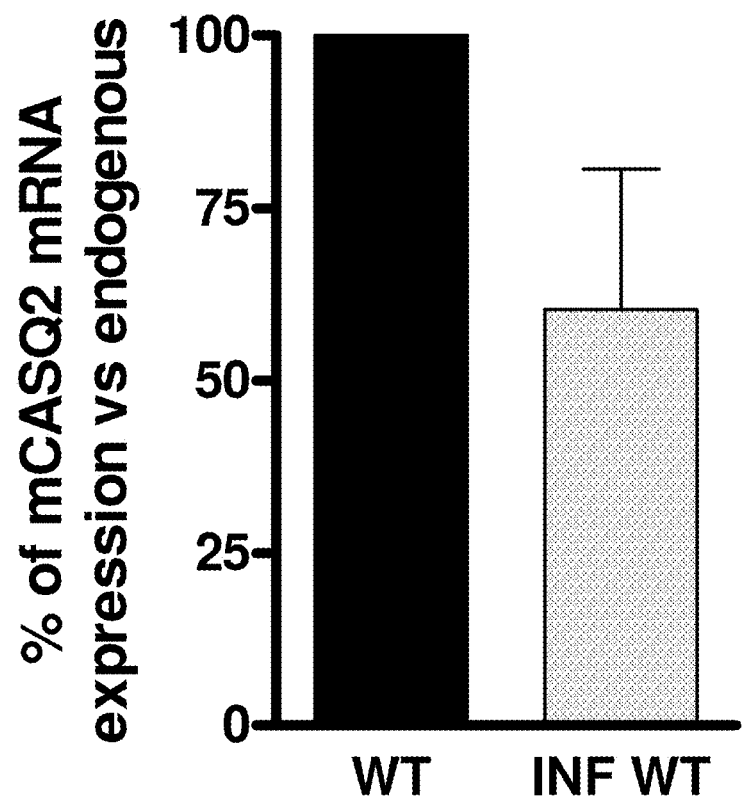

While the eGFP signal detection allowed to demonstrate the correct AAV2/9-mediated delivery of the transgene (CASQ2 in our case) into cardiac myocytes, the quantification of the expression levels was carried out through a series of in vitro assays on isolated myocytes. RealTime-PCR and immunoblot analysis provided quantification of expression at transcriptional and translational level of the mRNA and proteins. Quantitative RealTime PCR revealed an average of 60% (range 40-80%) as compared with WT normal levels of the murine calsequestrin mRNA in the infected mice (FIG. 2). Based on this encouraging result we than performed Immunoblot analysis in order to verify the correct expression of the cardiac calsequestrin in adult cardiomyocytes isolated from infected CASQ2-KO mice.

Figure 3:
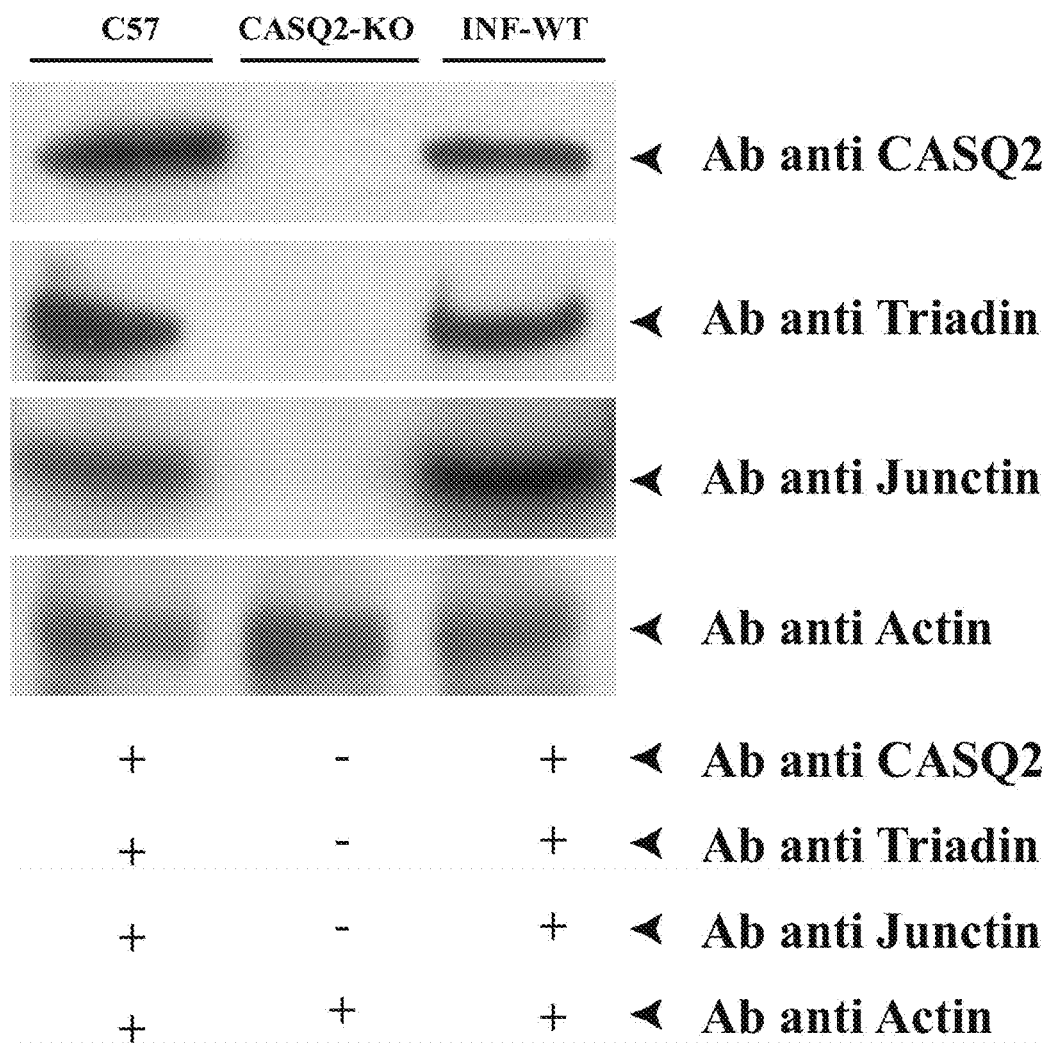

FIG. 3 depicts a typical Western blot experiments following these observations, showing that the viral transduction restored physiological levels of CASQ2 (FIG. 3). Furthermore, not only CASQ2, but also Tr and JnC are restored after infection with WT-mCASQ2 (FIG. 3). This strongly supports the concept of an interdependence of expression of these three pivotal proteins.

Figure 4:
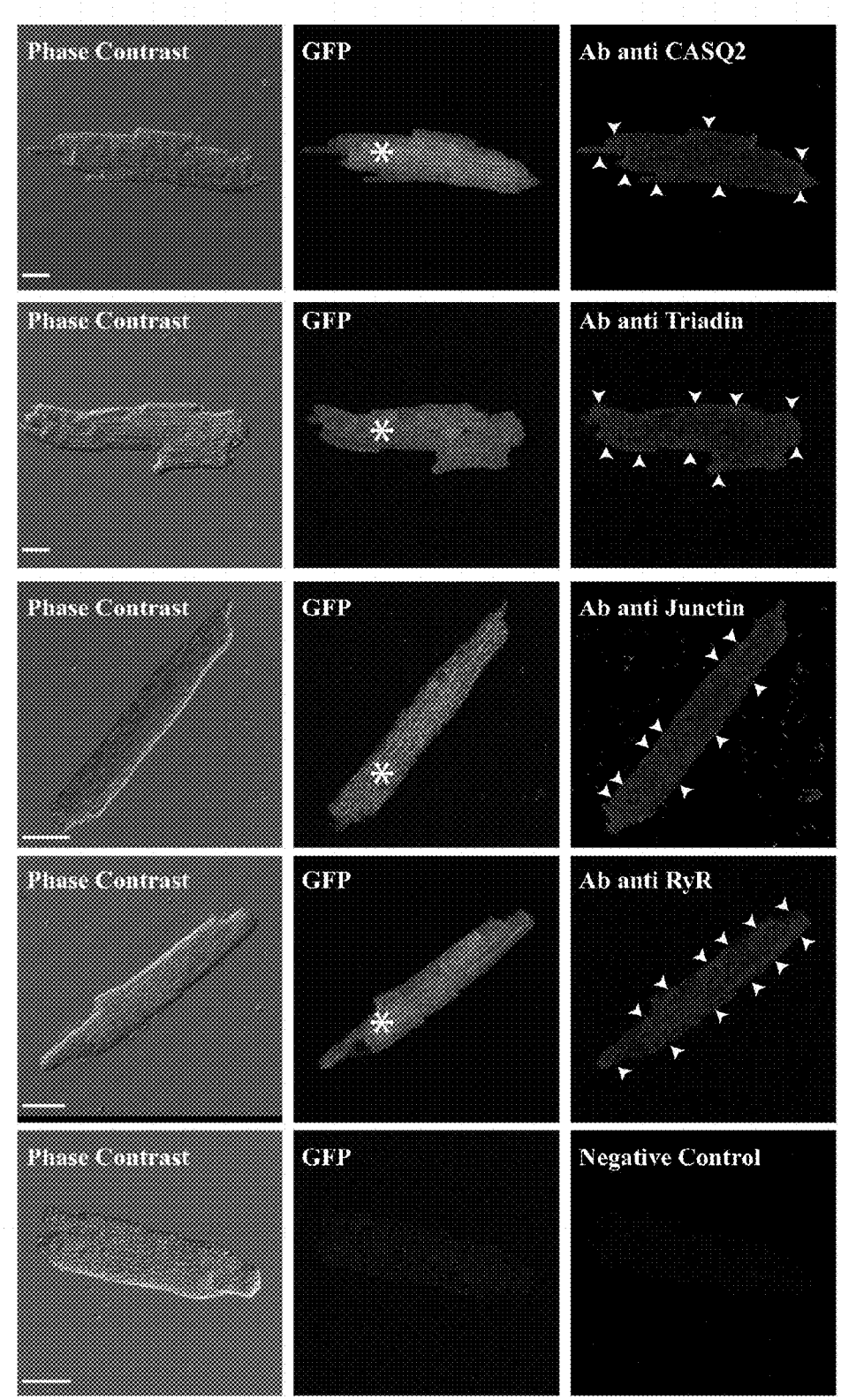

Using confocal microscopy, we confirmed the overall cellular localization of the "CRU" proteins, CASQ2, RyR2, Tr and Jnc in ventricular myocytes, in the WT-infected mice (FIG. 4).

Example 4

AAV2/9-WT-mCASQ2 Infection Restores the Functional Phenotype of CASQ2-KO Cells Our results suggest that CASQ2 viral gene transfer effectively leads to re-appearance of the exogenous CASQ2 in a remarkable 60% of null background cells. On the basis of this result it becomes rational to test the hypothesis that AAV2/9 mediated restoration of WT calsequestrin in CPVT mice can exert an antiarrhytmic effect.

From our previous investigation we knew that CPVT arrhythmias are caused by delayed after depolarizations (DADs) and triggered activity (TA) (4) at the level of the single cardiomyocyte. Using patch clamp techniques (in current clamp mode) we analyzed the development of the DADs and/or TA in basal condition and after adrenergical stimulation.

Figure 5:
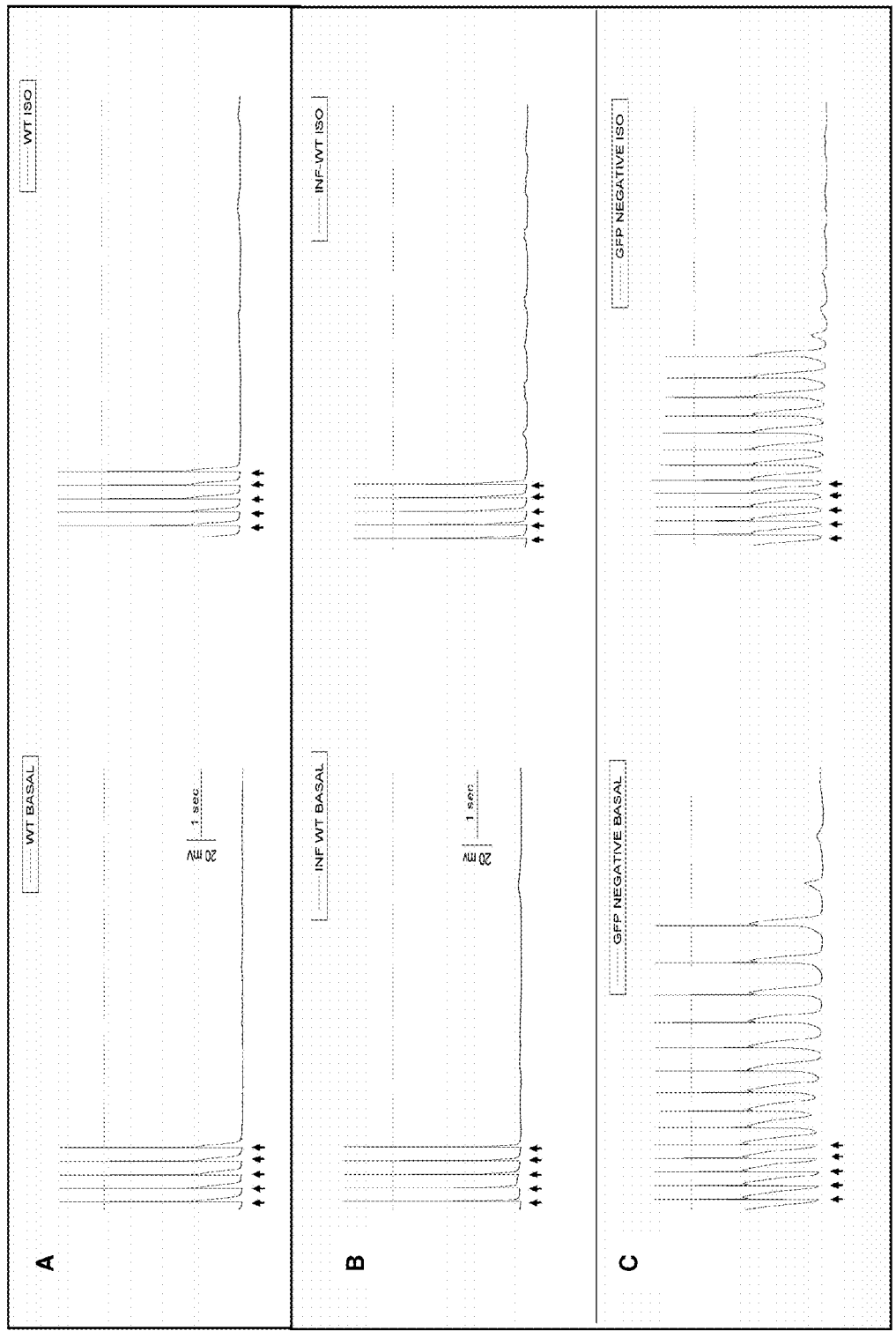
Figure 6:
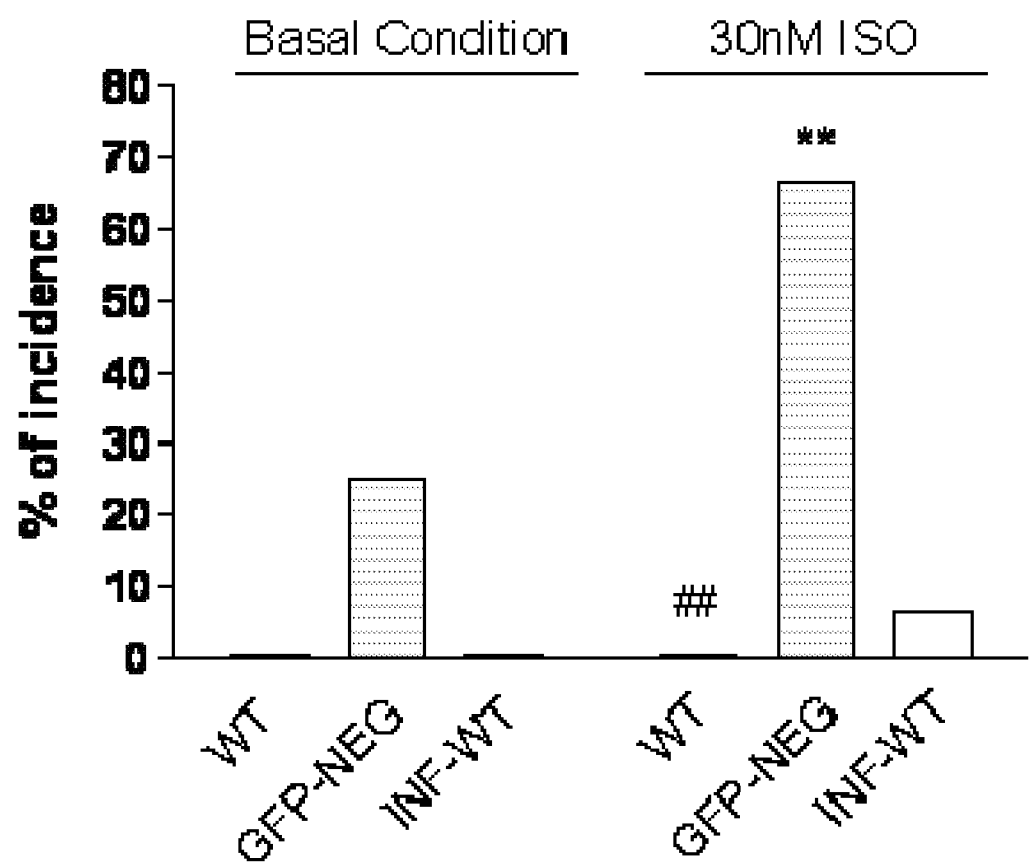

Epifluorescence signal (from the eGFP present in our viral construct) was used to differentiate between non-infected (i.e. non-fluorescent) and infected (i.e. green fluorescent) cells and to perform comparative assay of DAD and TA occurrence. Isolated myocytes were paced at 5 Hz frequency at 1.5-fold the diastolic threshold and action potential was continuously recorded. An average of 67% of GFP negative (non fluorescent) cells presented TA after ISO (30 nM) stimulation, while in the same experimental condition, only 6% of the GFP positive infected cells did. Importantly, the low incidence of TA in the infected cells is a remarkable reduction that resemble the TA registered in cells expressing the endogenous CASQ2 protein (FIG. 5-6).

Example 5

In Vivo Correction of the Dysfunctional Properties Observed in the CASQ2 KO Mice Thus the molecular and electrophysiological studies demonstrated a complete normalization of the phenotype at cellular level of the CASQ2 null mice after AAV2/9-WT-mCASQ2 infection, we extended our studies to in vivo characterization of the arrhythmogenic substrate in our CPVT model.

We used subcutaneous ECG telemeters to monitor and compare the incidence of arrhythmias in resting conditions, during and after exercise and adrenergic induced stress.

Under resting conditions CASQ2 null mice invariably (100% incidence) presented bidirectional ventricular tachycardia while neither WT nor Infected WT mice presented any ventricular arrhythmia.

Figure 7:
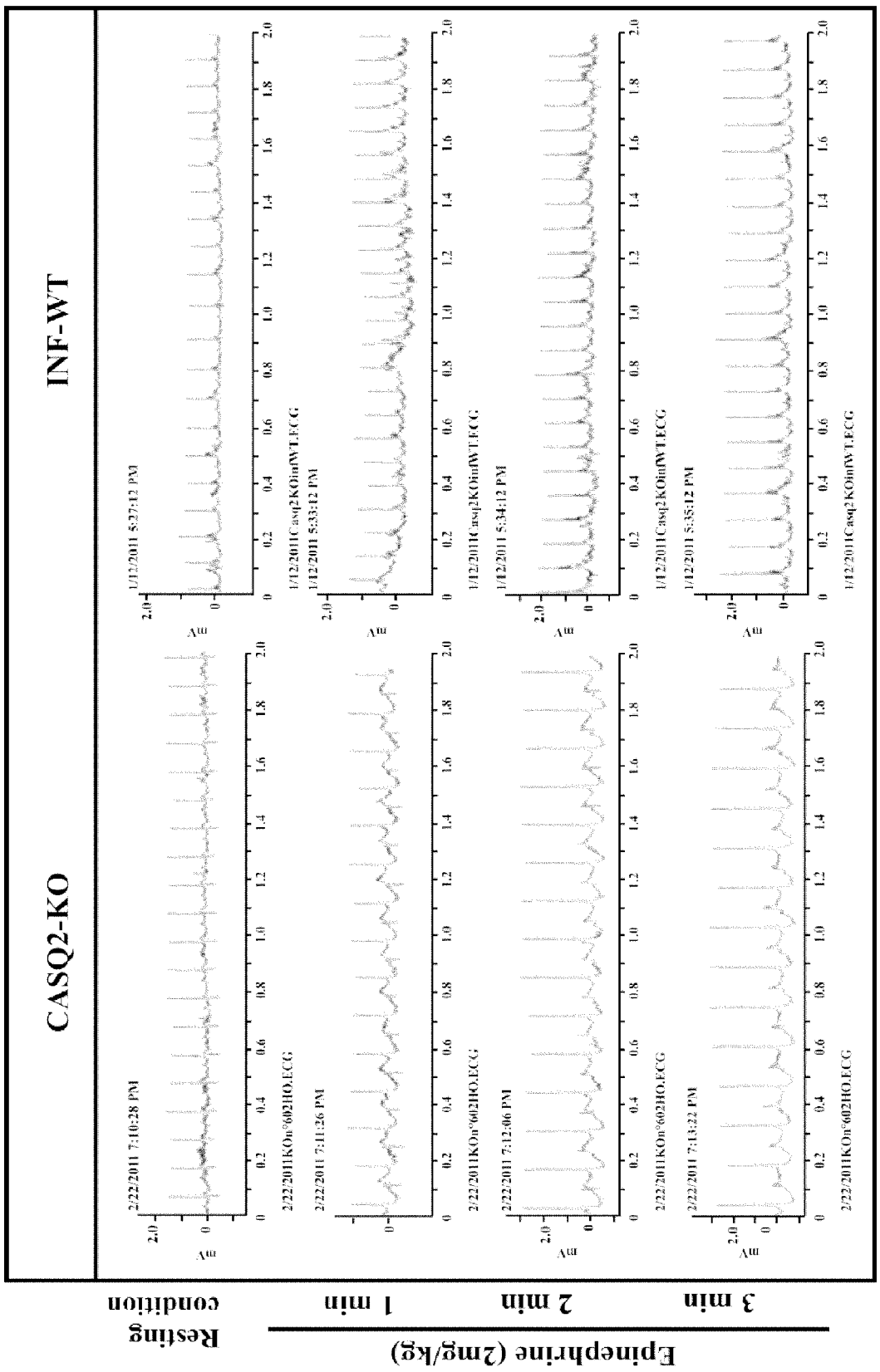

We than tested the inducibility of arrhythmias in the same groups of animals but during adrenergic stimulation as previously described (5). Mice were injected with epinephrine (2 mg/kg) which, again, induced the typical CPVT ventricular tachycardia in 100% of CASQ2 KO untreated mice. Conversely, no ventricular arrhythmias were detected in infected mice, just as it was found out in WT mice (Table 1 and FIG. 7).

TABLE 1

Incidence of Ventricular arrhythmias in the CASQ2-KO, WT and infected WT mice.

|  | Resting Condition | Epinephrine (2 mg/Kg) |
|---|---|---|
| CASQ2-KO | 5/5 | 5/5 |
| INFECTED WT | 0/5 | 0/5 |
| WT | 0/6 | 0/6 |

Viral CASQ2 gene transfer is highly effective in correcting all aspects of the functional derangements observed in the CASQ2 KO mice (Table 2)

TABLE 2

Summary of the biological effects of AAV2/9 WT-mCASQ2 infection on CASQ2-KO mice.

| | Functional Results | | |
|---|---|---|---|
| Mice | CRU proteins restoration (Tr-Jc) | Triger Activity (in vitro) | Ventricular Tachycardia (in vivo) |
| CASQ2-KO | − | + | + |
| CASQ2-WT | + | − | − |
| INF WT | + | − | − |

Materials and Methods

Animal Use

Animals were maintained and bred at the Charles River Laboratories in Calco, Italy, and transferred to the Maugeri Foundation for characterization of the phenotype. Animals were maintained and studied according to the protocols approved by the Animal Care and Use facility at the Maugeri Foundation. The adenovirus delivery was via intaperitoneal and intra-ocular injection of 100 µl of purified virus in neonatal mice with a 25 gauge syringe in pup mice before the $3^{rd}$ day of born (P1-P2).

Generation of Knock-out of CASQ2 in Mouse Model

The knock-out strain was generated by homologous recombination of the targeting vector with 129Sv/J embryonic stem cells genome. The linearized targeting vector was electroporated into 129Sv/J embryonic stem cells. The clone selected with G418 and gancyclovir was injected into C57BL/6NCrL blastocyts and transferred to pseudopregnant CD-1 females. Genotype was determined by sequencing of DNA extracted from tail biopsy specimens (DNeasy Tissue Kit, Qiagen).

Vector Design and Production

The coding sequence, without UTR sequences, of WT-murine CASQ2 (NM_009814.2) was cloned into pGEM-T-Easy vector (Promega). By enzymatic digestion, EcoRI, the insert corresponding to the WT-mCASQ2 was excised from the pGEM vector and subcloned in bis-cistronic pIRES vector (BD Biosciences, Cat. No: 631605, Clontech Palo Alto Calif., USA). Indeed, the fragment corresponding to the WT-mCASQ2 followed by the IRES sequence was subcloned via PCR amplification using specific primers (Forward: 5'-CACAGCGGCCGCACAATGAAGAGGATT-TACCTGCTCATGG-3'(SEQ ID No 7) and Reverse 5'-CGAAGCATTAACCCTCACTAAAGGG-3' (SEQ ID No 8) containing the Not I enzymatic site. The amplicon was inserted into the adenoviral backbone vector pAAV-2.1-eGFP, serotype 9 (containing: polyA sequence type BGH and CMV promoter), provided by the Adeno-Associated Virus (AAV) vector Core facility (Tigem, Napoli, Italy), by the enzymatic digestion with Not I. All the used plasmids were sequenced.

The AAV production was done in collaboration with the Tigem AAV Vector core facility (http://www.tigem.it/core-facilities/adeno-associated-virus-aav-vector-core). The AAV vectors were produced using a transient transfection of 3 plasmids in 293 cells: pAd helper, pAAV rep-cap (packaging), pAAV Cis (including our insert, WT-mCASQ2-IRES, cloned in the pAAV2.1-CMV-eGFP plasmid MCS). The vectors were purified by CsCl centrifugation and undergo quality control such as Real Time PCR and Dot Blot analysis for physical titer, or Comassie staining of SDS PAGE to evaluate the presence and purity of capsid proteins, the infectivity (eGFP+ cells/ml, only for CMV-eGFP preps) and the sterility (for preps to be used in large animals). The service returned with a viral preparation in PBS with a total yield$>1\times10^{12}$ genome copies. All AAV stocks were frozen at −80° C. in single vial and thawed during the surgical procedure.

Isolation of Adult Mice Ventricular Myocytes

Ventricular myocytes were isolated using an established enzymatic digestion protocol (4) from homozygous CASQ2 KO and homozygous CASQ2 KO infected with pAAV2.1-eGFP-WT-mCASQ2 and wild-type (WT) mice (20 weeks) of either sex.

Quantitative Real-Time PCR

Real-time PCR was performed using the CFX96 Real-Time PCR Detection System and analyzed using the Bio-Rad CFX Manager software package (Bio-Rad Laboratories, Inc., USA). Briefly, total RNA was purified with Rneasy mini kit (Qiagen) from myocyets derived from adult CASQ2 knock-out mice and homozygous CASQ2 knockout mice infected with pAAV2.1-, serotype 9, -eGFP-WT-mCASQ2 and C57/BL6 mice as WT mice. Absorbance at 260 nm (A260) was measured for each RNA sample using the NanoDrop (ND-1000) spectrophotometer (NanoDrop Technologies, Wilmington, Del., USA). A total amount of 0.25 µg template RNA per reaction was taken for RT-PCR assay performed with iScript cDNA Synthesis kit (Bio-Rad Laboratories, Inc., USA). Quantitative PCR analysis was performed in optical 96-well plates using CFX96 detection module (Bio-Rad Laboratories, Inc.). All samples were analyzed in triplicate with SsoFast EvaGreen Supermix using specific primer mix (Forward:5'-ATGAAGAGGATTTACCTGCTCATG-3' (SEQ ID No 3), Reverse: 5'-CAAGCTCCAGTACAATCTC-CTTC-3' (SEQ ID No 4) and 100 ng of cDNA template. Values for threshold cycle (Ct) determination were generated automatically by the Bio-Rad CFX Manager software 1.5. GAPDH was used as internal reference using the following primers: Forward: 5'-GTATGACTCCACTCACGGCAA-3' (SEQ ID No 5) and Reverse: 5'-GCTTCCCATTCTCGGC-CTTG-3' (SEQ ID No 6).

Immunoblotting

Isolated ventricular myocytes have been processed in RIPA buffer (Thermo scientific) and total proteins extracted. Total proteins (20 µg/sample, quantified by the BCA assay) were resolved by SDS-gel electrophoresis, Novex 4-12% BisTris gradient gels using MES buffer (Invitrogen), and blotted on nitrocellulose membranes using a submarine system (Invitrogen). The membranes were probed with different antibodies: anti-CASQ2 (PA1-913, ABR), anti-Triadin (sc-33393, Santa Cruz) and anti-Junctin (a kind gift from Dr Knollmann) and anti-Actin (sc-1616-R, Santa Cruz) as reference protein. Secondary antibodies were conjugated with HRP (1:3000, Promega). C57/BL6 derived cells were used as positive control. Specific signals were developed using the Supersignal West Pico Chemiluminescent substrate (Pierce) and detected using X-ray films (Kodak).

Immunofluorescence

Isolated adult cardiomyocytes were fixed on coverslips in 4% paraformaldehyde for 10 minutes at room temperature. Coverslips were then washed in PBS with gentle shaking. Fixed cells were permeabilized with 0.2% Triton X-100 in PBS for 10 minutes at room temperature. All the cells were kept in blocking solution (10% BSA in PBS) for 1 hour at 37° C. Coverslips were then incubated for 1 hour at 37° C. with a primary antibody. The analysis was performed using following antibodies: anti-RyR2 (MA3-916, ABR), anti-CASQ2 (PA1-913, ABR), anti-Triadin (sc-33393, Santa Cruz) and anti-Junctin. After washing in PBS, cells were incubated with Dy-Light-conjugated 594-conjugated donkey anti-mouse/rabbit IgG secondary antibodies for 1 hour at 37° C. The cells were washed several times in PBS and mounted on slides with mounting medium (Vectashield H-1400, Vector Laboratories, Inc, CA). Confocal microscopy was performed with a Leica TCS-SP2 digital scanning confocal microscope equipped with a HCX PL APO 40×/numerical aperture=1.25 oil immersion objective. We used the 488-nm Argon laser line for excitation of eGFP and He/Ne laser line for excitation of Dy-Light-conjugated 594-conjugated donkey anti-mouse IgG (detected at 580-630 nm). The pinhole diameter was kept at Airy 1. Images were exported to Adobe Photoshop CS3 (Adobe Systems, Mountain View, Calif.).

Electrophysiological Recordings in Isolated Ventricular Myocytes

Cardiomyocytes were seeded on a glass bottom perfusion chamber mounted on the stage of an inverted microscope. After 5 minutes, the myocytes were bathed with the solution containing (in mmol/L): 140 NaCl, 4 KCl, 2 $CaCl_2$, 1 $MgCl_2$, 10 HEPES, and 5 glucose, pH 7.4, with NaOH. A thermostatically controlled heating ring surrounding the dish was used to maintain the bath solution at 35° C. Transmembrane potentials were recorded in whole cell current clamp mode using a MultiClamp 700B amplifier (Axon Instruments). Patch electrodes were pulled from borosilicate glass (WPI, Inc.) on a P-97 horizontal puller (Sutter Instruments). The electrodes had a resistance of 2 to 3 MΩ when filled with patch electrode solutions containing (in mmol/L): 120 potassium aspartate, 20 KCl, 1 MgCl$_2$, 4 Na$_2$ATP, 0.1 GTP, 10 HEPES, 10 glucose, pH 7.2, with NaOH. All signals were acquired at 10 kHz (Digidata 1322A, Axon Instruments) and analyzed with the use of personal computer running pCLAMP version 9.2 software (Axon Instruments). Only quiescent, calcium-tolerant, rod-shaped cells with clear cross striations and a resting potential of less than or equal to −80 mV were used for electrophysiological recordings. Myocytes were electrically stimulated by intracellular current injection through patch electrodes using depolarizing pulses with duration of 3 ms and amplitude of 1.5 times the minimal current needed to evoke and action potential. The liquid junction potential between pipette and bath solution was calculated with pCLAMP software and corrected after experiments.

ECG Monitoring, Exercise Stress Testing, and Drug Testing

ECG radiotelemetry monitors (Data Sciences International) were implanted subcutaneously under general anaesthesia (Avertin 0.025 mg/kg). Body temperature was maintained at 37° C. by use of a thermally controlled heating pad (Harvard Apparatus). After 72 hours of recovery from surgery, phenotype characterization was performed. First, basal ECG was recorded for 24 hours to asses for the presence of spontaneous arrhythmias, the animals were then exercised on a treadmill until exhaustion (15-20 min). After one day of recovery, susceptibility to adrenergically-induced arrhythmias was tested by epinephrine injection (2 mg/kg I.P.)

All animals were freely moving while ECG recordings were performed.

References

1. Priori S G, Napolitano C, Colombo B, Memmi M, Bloise R. Mutations of the cardiac Ryanodine receptor (RyR2) gene are associated to heterogeneous clinical phenotypes and high lethality. *Circulation* 2001; 104(suppl II):335.
2. Lahat H, Pras E, Olender T, Avidan N, Ben Asher E, Man O, Levy-Nissenbaum E, Khoury A, Lorber A, Goldman B, Lancet D, Eldar M. A missense mutation in a highly conserved region of CASQ2 is associated with autosomal recessive catecholamine-induced polymorphic ventricular tachycardia in Bedouin families from Israel. *Am J. Hum. Genet.* 2001; 69:1378-1384.
3. Cerrone M, Colombi B, Santoro M, Raffale di Barletta M, Scelsi M, Villani L, Napolitano C, Priori S G. Bidirectional Ventricular Tachycardia and Fibrillation Elicited in a Knock-In Mouse Model Carrier of a Mutation in the Cardiac Ryanodine Receptor (RyR2). *Circulation Research* 2005; 96:e77-e82.
4. Liu N, Colombi B, Memmi M, Zissimopoulos S, Rizzi N, Negri S, Imbriani M, Napolitano C, Lai F A, Priori S G. Arrhythmogenesis in Catecholaminergic Polymorphic Ventricular Tachycardia. Insights From a RyR2 R4496C Knock-In Mouse Model. *Circulation Research* 2006; 99:292-298.
5. Rizzi N, Liu N, Napolitano C, Non A, Turcato F, Colombi B, Bicciato S, Arcelli D, Bigioggera M, Scelsi M, Villani L, Volpe P, Priori S G. Unexpected structural and functional consequences of the R33Q homozygous mutation in cardiac calsequestrin: a complex arrhythmogenic cascade in a knock in mouse model. *Circulation Research* 2008; 103:298-306.
6. Horowitz J D, Rosenson R S, McMurray J J, Marx N, Remme W J. Clinical Trials Update AHA Congress 2010. Cardiovasc Drugs Ther 2010; 25:69-76.
7. Bish L T, Morine K, Sleeper M M, Sanmiguel J, Wu D, Gao G, Wilson J M, Sweeney H L. Adeno-associated virus (AAV) serotype 9 provides global cardiac gene transfer superior to AAV1, AAV6, AAV7, and AAV8 in the mouse and rat. Hum Gene Ther. 2008; 19(12):1359-68.
8. Knollmann B C, Chopra N, Hlaing T, Akin B, Yang T, Ettensohn K, Knollmann B E, Horton K D, Weissman N J, Holinstat I, Zhang W, Roden D M, Jones L R, Franzini-Armstrong C, Pfeifer K. Casq2 deletion causes sarcoplasmic reticulum volume increase, premature Ca2+ release, and catecholaminergic polymorphic ventricular tachycardia. *J Clin Invest.* 2006; 116:2510-2520.

The invention claimed is:

1. A method for the treatment of recessive catecholaminergic polymorphic ventricular tachycardia comprising: delivering a CASQ2 gene into a cardiac cell, wherein the CASQ2 gene encodes a calsequestrin protein having a sequence with 95% or more homology with the sequence of a protein encoded by the nucleotide sequence as set forth in SEQ ID NO:1 or SEQ ID NO:2, and wherein said delivery of a CASQ2 gene restores the intracellular $Ca^{2+}$ storage and $Ca^{2+}$ fluxes and has the effect of alleviating recessive catecholaminergic polymorphic ventricular tachycardia.

2. The method according to claim 1, wherein the CASQ2 gene is inserted in a vector.

3. The method according to claim 1, wherein the CASQ2 gene is inserted in a viral vector.

4. The method according to claim 1, wherein the CASQ2 gene is inserted in a serotype 9 adeno-associated viral vector.

5. The method according to claim 1, wherein the CASQ2 gene encodes a calsequestrin protein having a sequence with 95% or more homology with the sequence of a protein encoded by the nucleotide sequence as set forth in SEQ ID NO:1.

6. The method according to claim 1, wherein the CASQ2 gene encodes a calsequestrin protein having a sequence with 95% or more homology with the sequence of a protein encoded by the nucleotide sequence as set forth in SEQ ID NO:2.

7. The method according to claim 1, wherein the CASQ2 gene encodes a calsequestrin protein having a sequence encoded by the nucleotide sequence as set forth in SEQ ID NO:1.

8. The method according to claim 1, wherein the CASQ2 gene encodes a calsequestrin protein having a sequence encoded by the nucleotide sequence as set forth in SEQ ID NO:2.

9. The method according to claim 1, wherein the CASQ2 gene comprises a sequence having 95% or more homology with the nucleotide sequence as set forth in SEQ ID NO:1.

10. The method according to claim 1, wherein the CASQ2 gene comprises a sequence having 95% or more homology with the nucleotide sequence as set forth in SEQ ID NO:1.

* * * * *

SEQUENCE LISTING

```
<160> NUMBER OF SEQ ID NOS: 8

<210> SEQ ID NO 1
<211> LENGTH: 1248
<212> TYPE: DNA
<213> ORGANISM: Mus musculus

<400> SEQUENCE: 1
atgaagagga tttacctgct catggtgggg gtttatctgc tgtccctgag cggggcagaa      60
gaggggctga acttccccac gtacgatggg aaagaccgag tggtcagcct ttctgagaag     120
aacctcaagc agatgttgaa gagatatgat ttgctctgtc tctattacca cgaacctgtg     180
tcttcagaca aggtctcaca aaaacagttc cagctgaagg agattgtact ggagcttgtg     240
gcccaggtcc tggaacataa aaacataggc tttgtgatgg tggattcgag gaaagaggcc     300
aagcttgcta agaggctggg attcagtgaa gaaggaagcc tgtatgttct gaagggtgac     360
cgcacgattg agtttgacgg ggagttcgca gcagatgtct tagtggaatt tctcttggat     420
ctcattgaag acccagtgga gatcgtgaat aacaagctgg aggtccaggc ctttgagcgc     480
atcgaggacc agaccaagct ccttggcttc ttcaagaatg aggactcaga atattacaaa     540
gcattccaag aggcagctga acacttccag ccttacatca agttctttgc caccctttgac    600 aaggcggtgg caaagaagtt atccttgaag atgaacgaag ttggcttcta tgagccattt     660
```

```
atggatgagc ccaacgtcat ccctaacaaa ccgtacacag aagaggagct tgtggagttt      720
gtgaaggaac atcaaagacc caccctacgt cgcttgcgcc cagaggacat gtttgaaaca      780
tgggaagacg acttgaatgg gatccacatc gtggcctttg cggagaagag tgacccagat      840
ggctatgagt tcctagagat cctgaaacag gttgcccggg acaacactga caatcctgac      900
ttgagcatct tgtggattga cccagatgac tttccactgc ttgttgctta ctgggagaag      960
actttcaaga ttgacctgtt caagccacag attggggtgg tgaatgtaac cgatgctgac     1020
agtatctgga tggagatccc agatgatgac gacctgccca cagctgagga gctggaagac     1080
tggattgaag atgtgctttc tggaaagatc aacactgaag atgatgacaa tgaagatgaa     1140
gatgatgatg gtgatgacaa cgatgacgat gatgatgacg acgatgataa tgataattct     1200
gatgaggata tgaagacagt gatgatgac gatgatgacg atgaatag                   1248

<210> SEQ ID NO 2
<211> LENGTH: 1200
<212> TYPE: DNA
<213> ORGANISM: Homo sapiens

<400> SEQUENCE: 2
atgaagagaa ctcacttgtt tattgtgggg atttattttc tgtcctcttg cagggcagaa       60
gaggggctta atttccccac atatgatggg aaggaccgag tggtaagtct ttccgagaag      120
aacttcaagc aggttttaaa gaaatatgac ttgctttgcc tctactacca tgagccggtg      180
tcttcagata aggtcacgca aaacagttc caactgaaag aaatcgtgct tgagcttgtg      240
gcccaggtcc ttgaacataa agctataggc tttgtgatgg tggatgccaa gaaagaagcc      300
aagcttgcca gaaactgggt ttttgatgaa gaaggaagcc tgtatattct taagggtgat      360
cgcacaatag agtttgatgg cgagtttgca gctgatgtct tggtggagtt cctcttggat      420
ctaattgaag acccagtgga gatcatcagc agcaaactgg aagtccaagc cttcgaacgc      480
attgaagact acatcaaact cattggcttt ttcaagagtg aggactcaga atactacaag      540
gcttttgaag aagcagctga acacttccag ccttacatca aattctttgc caccttgac      600 aaaggggttg caagagaaatt atcttgaag atgaatgagg ttgacttcta tgagccattt      660
atggatgagc ccattgccat ccccaacaaa ccttacacag aagaggagct ggtggagttt      720
gtgaaggaac accaaagacc cactctacgt cgcctgcgcc cagaagaaat gtttgaaaca      780
tgggaagatg atttgaatgg gatccacatt gtggcctttg cagagaagag tgatccagat      840
ggctacgaat tcctggagat cctgaaacag gttgcccggg acaatactga caccccgat      900 ctgagcatcc tgtggatcga cccggacgac tttcctctgc tcgttgccta ctgggagaag      960
actttcaaga ttgacctatt caggccacag attggggtgg tgaatgtcac agatgctgac     1020
agtgtctgga tggagattcc agatgatgac gatcttccaa ctgctgagga gctggaggac     1080
tggattgagg atgtgctttc tggaaagata aacactgaag atgatgatga agatgatgat     1140
gatgatgata attctgatga gaggataat gatgacagtg atgacgatga tgatgaatag     1200

<210> SEQ ID NO 3
<211> LENGTH: 40
<212> TYPE: DNA
<213> ORGANISM: Mus musculus

<400> SEQUENCE: 3
cacagcggcc gcacaatgaa gaggatttac ctgctcatgg                             40
```

```
<210> SEQ ID NO 4
<211> LENGTH: 25
<212> TYPE: DNA
<213> ORGANISM: Mus musculus

<400> SEQUENCE: 4
cgaagcatta accctcacta aaggg                                               25

<210> SEQ ID NO 5
<211> LENGTH: 24
<212> TYPE: DNA
<213> ORGANISM: Mus musculus

<400> SEQUENCE: 5
atgaagagga tttacctgct catg                                                24

<210> SEQ ID NO 6
<211> LENGTH: 23
<212> TYPE: DNA
<213> ORGANISM: Mus musculus

<400> SEQUENCE: 6
caagctccag tacaatctcc ttc                                                 23

<210> SEQ ID NO 7
<211> LENGTH: 21
<212> TYPE: DNA
<213> ORGANISM: Mus musculus

<400> SEQUENCE: 7
gtatgactcc actcacggca a                                                   21

<210> SEQ ID NO 8
<211> LENGTH: 20
<212> TYPE: DNA
<213> ORGANISM: Mus musculus

<400> SEQUENCE: 8
gcttcccatt ctcggccttg                                                     20
```